United States Patent
Yu et al.

(10) Patent No.: US 6,727,288 B2
(45) Date of Patent: Apr. 27, 2004

(54) METHOD FOR TREATING BONE FRACTURE

(75) Inventors: Kai Yu, Beijing (CN); Zhiwen Wang, Beijing (CN); Xiangguo Dai, Beijing (CN)

(73) Assignee: Juneng Industry Co., Ltd., Beijing (CN)

( * ) Notice: Subject to any disclaimer, the term of this patent is extended or adjusted under 35 U.S.C. 154(b) by 21 days.

(21) Appl. No.: 10/039,194

(22) Filed: Dec. 31, 2001

(65) Prior Publication Data

US 2002/0169210 A1 Nov. 14, 2002

(30) Foreign Application Priority Data

Mar. 7, 2001 (CN) .......................................... 01119870 A

(51) Int. Cl.$^7$ ................................................. A61K 31/13
(52) U.S. Cl. ....................................... 514/663; 514/671
(58) Field of Search ................................... 514/663, 671

(56) References Cited

U.S. PATENT DOCUMENTS

| | | | | | |
|---|---|---|---|---|---|
| 5,622,935 A | * | 4/1997 | Koyama et al. | ............... | 514/21 |
| 5,656,598 A | * | 8/1997 | Dunstan et al. | ................ | 514/12 |
| 5,804,570 A | * | 9/1998 | Santora et al. | ............... | 514/108 |
| 6,077,872 A | * | 6/2000 | Yu et al. | ...................... | 514/663 |
| 6,313,170 B1 | * | 11/2001 | Yu et al. | ...................... | 514/557 |
| 6,548,687 B1 | * | 4/2003 | Yu et al. | ......................... | 556/61 |

FOREIGN PATENT DOCUMENTS

| | | | |
|---|---|---|---|
| CN | 1143464 A | * | 2/1997 |
| CN | 1215592 A | * | 5/1999 |
| CN | 1305751 A | * | 8/2001 |

* cited by examiner

*Primary Examiner*—Zohreh Fay
*Assistant Examiner*—Brian-Yong S. Kwon
(74) *Attorney, Agent, or Firm*—Alston & Bird LLP

(57) ABSTRACT

The present invention relates to a method for treating or preventing bone fracture, which comprises administering an effective amount of calcium L-threonate to a subject in need of such prevention or treatment. It had been found from experiments that calcium L-threonate could not only promote proliferation, differentiation and mineralization of osteoblasts, but also could promote the expression of collagen I mRNA of osteoblasts cultured in vitro. Accordingly it facilitated bone fracture healing and increased bone density and mechanical performance, so as to prevent or treat bone fracture.

6 Claims, No Drawings

METHOD FOR TREATING BONE FRACTURE

BACKGROUND OF THE INVENTION

The present invention relates to a method for treating or preventing bone fracture, and in particular relates to a method for treating or preventing bone fracture by administering an effective amount of calcium L-threonate to a subject in need of such prevention or treatment.

Bone fracture is a disruption of structure continuity of a bone, and it is a common surgical disease. Bone fracture can be classified into traumatic fracture and pathological fracture. Traumatic fracture is caused by external force, and pathological fracture is due to the pathological change of bone itself, such as senile osteoporosis, along with a certain degree of external force on the bone.

Traditionally, bone fracture healing is classified into four phases: 1) inflammation, 2) soft callus, 3) hard callus and 4) remodeling. The inflammation phase is an immediate response following bone fracture. At that time, a hematoma occurs at the fracture site and the adjacent tissues, and an acute inflammation response occurs immediately, which is manifested by blood vessels dilating, and the effusing of plasma and leukocytes. The soft callus phase is a period from the disappearance of swelling and pain to the connection of fibers or cartilage tissue at the fracture site, during which the hematoma is organized, osteoclasts remove residual necrotic bone, and intramembranous ossification begins to form. Its characteristic is that blood vessels increase greatly, capillary vessels grow into callus, and cells are very abundant. The hard callus phase is a period from the adhesion of soft callus at the fracture site to the formation of new bone. This phase corresponds to the period of bone fracture healing in clinic or X-ray representation. It generally takes three to four months, during which callus changes to fibrous bone from fibrocartilage tissue, and membranous bone forms between the fracture sites. Their remolding phase is a process in which the fracture sites are connected by newly born bones and gradually adapt to new functions.

Bone fracture healing is a very unique process of tissue repair program. It is different from the repair of other tissues, since the result of other tissue repair is cicatrization, whereas bone repair is not by cicatrization but by regeneration of bone. Therefore the proliferation of osteoblasts plays a crucial role in bone fracture healing.

In addition, Lane classified bone fracture healing from the view point of biochemistry: 1) mesenchyma phase, when collagen I, II and III is synthesized; 2) cartilaginous phase, when collagen II is predominant; 3) cartilage and osteoid phase, when collagen I and II is predominant; 4) osteogenesis phase, when collagen I is predominant. Therefore, the synthesis of collagen plays a very important role in bone fracture healing.

Now it is generally believed that conventional calcium formulations have no significant effects on promoting bone fracture healing. In addition, other drugs that can significantly promote bone fracture healing are not found yet. The major treatment of bone fracture is still the combination of the following three traditional means: 1) restoration of bone fracture; 2) fixation; 3) functional exercise.

Therefore, an object of the present invention is to provide a method for preventing or treating bone fracture, which comprises administering an effective amount of calcium L-threonate to a subject suffering from bone fracture.

It is another object of the present invention to provide a pharmaceutical composition for preventing or treating bone fracture, comprising an effective amount of calcium L-threonate.

It is a further object of the present invention to provide the use of calcium L-threonate in the preparation of a pharmaceutical composition for treating or preventing bone fracture.

It is still another object of the present invention to provide calcium L-threonate usable for preventing or treating bone fracture.

It is a further object of the present invention to provide use of calcium L-threonate for preventing or treating bone fracture.

In view of the above factors that facilitate bone fracture healing, the present inventors studied the stimulation effects of calcium L-threonate on proliferation, differentiation of osteoblasts and bone formation, as well as the effects of calcium L-threonate on promoting synthesis of collagen I. The result is astonishing that calcium L-threonate can not only facilitate the proliferation, differentiation and mineralization of osteoblasts, but also can enhance mRNA expression of collagen I in osteoblasts cultured in vitro. By this means, it can promote bone fracture healing and treat bone fracture, whereby the inventor completed the present invention.

Meanwhile, through the above-mentioned effects, calcium L-threonate can increase bone density and mechanical properties, so as to prevent bone fracture, especially pathological fracture, such as the fracture caused by senile osteoporosis.

BRIEF SUMMARY OF THE INVENTION

The present invention relates to a method for treating bone fracture, which comprises administering an effective amount of calcium L-threonate to a subject suffering from bone fracture. As used herein, the term "bone fracture" includes but is not limited to traumatic fracture and pathological fracture.

The present invention also includes a method for preventing bone fracture, preferably traumatic fracture and pathological fracture, more preferably traumatic fracture, which comprises administering an effective amount of calcium L-threonate to a subject suffering from bone fracture.

The present invention also relates to a pharmaceutical composition for preventing or treating bone fracture, comprising an effective amount of calcium L-threonate.

The present invention further includes the use of calcium L-threonate in the preparation of a pharmaceutical composition for treating or preventing bone fracture.

The present invention also relates to calcium L-threonate usable for preventing or treating bone fracture.

The present invention also includes use of calcium L-threonate for preventing or treating bone fracture.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The calcium L-threonate of the present invention is white powder, scarcely with odor. It is soluble in water but insoluble in alcohol, ether and chloroform and has a formula $C_8H_{14}O_{10}Ca$ and a chemical structural formula represented by:

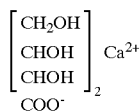

The compound can be prepared by: a certain amount of L-ascorbic acid (Vc) was added to water and dissolved, then calcium carbonate was slowly added into the mixture with stirring. To the above mixture, hydrogen peroxide was added dropwise at a temperature between 10° C. and 60° C. and maintained the temperature for 1–4 hours at 40–80° C. After active charcoal was added, the mixture was filtered. The filtrate was concentrated at a temperature between 30° C. and 90° C. and crystallized at ambient temperature. The crystal was dried at a temperature of 50–100° C.

In the above process of preparing calcium L-threonate, the addition of calcium carbonate must be carried out very slowly to avoid loss of material the container due to production of carbon dioxide gas.

The above process of preparing calcium L-threonate may further comprise the operation of washing the cake obtained by filtering the mixture that had been treated with active charcoal, twice with hot water of 80° C. and the operation of concentrating the combined washes and filtrate.

The above process of preparing calcium L-threonate is advantageous for its reasonable procedure, simple operation, good yield as high as 90% and high purity of product. The preparation method of calcium L-threonate is described in U.S. Pat. No. 6,077,872, issued on Jun. 20, 2000 to Kai Yu et al., which is incorporated herein by reference.

Of course, the calcium L-threonate of the present invention may also be prepared by the other methods known in the prior art.

The calcium L-threonate of the present invention may be administered orally. The calcium L-threonate of the present invention may be used in various forms of formulations, such as tablets, capsules and other forms of pharmaceutically acceptable compositions.

The pharmaceutical composition according to the present invention contains a certain amount of calcium L-threonate as an active ingredient, along with a pharmaceutically acceptable carrier, which can be various carriers that have been widely used in medicaments in the prior art such as excipients. The pharmaceutical composition of the present invention can be prepared by the methods known in the art, such as mixing, pelleting and tabletting.

The pharmaceutical composition of the present invention may also contain other optional ingredients that can be used in pharmacology, such as perfumes, colorants and sweetening agents, etc. The preferred pharmaceutical composition of the present invention contains 60%, preferably 80%, more preferably 90% by weight of calcium L-threonate with other excipients and optional components as make-ups.

The dosage of calcium L-threonate may vary depending on the age of patients. As guidance, the dosage of calcium L-threonate for an adult is typically between 0.5 g and 12 g per day, preferably between 3 g and 7 g per day. For children, the dosage may be decreased according to their weights.

The experiments of pharmacokinetics of calcium L-threonate in animal bodies demonstrated that the absorption metabolism of calcium L-threonate in rat satisfied the One-Chamber model. The absorption of calcium L-threonate was relatively slower but more complete, the peak of serum calcium concentration was later ($T_{max}$=0.79 hrs), its half-life was longer ($T_{1/2}$=4.45 hrs) than those of other calcium agents such as calcium gluconate, calcium acetate, and calcium carbonate. Calcium L-threonate can stay in serum for a longer time at a higher level. The area under the curve (AUC) equals to 191.75 g/(ml.hr). The pharmacokinetic test of calcium L-threonate is described in U.S. Pat. No. 6,077,872, issued on Jun. 20, 2000 to Kai Yu et al., which is incorporated herein by reference.

In the present invention, we have studied the effects of calcium L-threonate on stimulation of proliferation, differentiation of osteoblasts cultured in vitro and bone formation. The details of this study are described in Experiment I hereinafter.

In the present invention, we have also studied the influence of calcium L-threonate on ALP activity of $OB_2$. The details of this study are described in Experiment II hereinafter.

The following experiments are intended to illustrate, but in no way limit the scope of the present invention.

Experiment I

Effects of Calcium L-Threonate on Stimulation of Proliferation, Differentiation of Osteoblasts Cultured in vitro and Bone Formation In order to provide cytologic basis of calcium L-threonate to facilitate osteoblast proliferation and increase bone mass, the present test studied the effect of calcium L-threonate on stimulation of bone formation function of osteoblast by using the method of culturing osteoblasts in vitro. The calvaria of newborn SD rat were excised, and osteoblasts were isolated and seeded at a cell concentration of $1\times10^4$/ml in the culture medium containing 10 wt % of NCS-MEM. The second generation of secondary cells were tested for pharmacodynamics. The results showed that calcium L-threonate with a concentration of $10^{-9}$–$10^{-3}$ mol/L had the effects of promoting proliferation of osteoblast; that calcium L-threonate with a concentration of $10^{-3}$ mol/L had significant effects on stimulating cell activity and mineralization nodule formation and had certain effects on promoting alkaline phosphatase (referred to herein below as ALP) activity and mineralization nodule formation.

MATERIALS AND METHODS

1) Sampling: after a newborn (within 24 hours) SD rat was disinfected, the calvaria were excised under sterilization conditions. The calvaria were predigested by 0.25% trypsin for 10–15 minutes firstly, then oscillated and digested by 0.1% collagenase II at 37° C. for 60 minutes. The cells were collected by centrifugation at 1000 rpm.

2) Cell culture: The isolated cells were inoculated into culture flask at a concentration of $1\times10^4$/cm$^2$, wherein the culture solution is 10% of NCS-MEM. The cells were cultured in an incubator with 5% $CO_2$ at 37° C., then passaged until half confluence. The second generation of secondary cells ($OB_2$) were tested for pharmacodynamics.

3) Medicines: Each test medicine was formulated at a concentration of 0.1 mol/L, and sterilized by high pressure for later use.

1.55 g of calcium L-threonate was dissolved in 50 ml of deionized water by heating. 2.24 g of calcium gluconate was dissolved in 50 ml of deionized water at room temperature. The control group was deionized water.

4) Observation index (1) Cell Proliferation $OB_2$ were inoculated into 24 well COSTOR culture plate at a density of $6 \times 10^3$ per well. 24 hours later, the above culture solution was replaced by culture solution containing varying concentrations of medicines ranging from $10^{-9}$ to $10^{-3}$ mol/L. 72 hours after adding medicines, the cells were tested through Labsystems Multiskan MS (Finland) )ELISA analyzer by MTT method. OD value at 570 nm was used to reflect cell proliferation. The result was compared with that of control group.

(2) Determination of ALP Activity $OB_2$ was inoculated into 24 well COSTOR culture plate at a density of $2 \times 10^4$ per well. 24 hours later, the above culture solution was replaced by medium containing medicines. Then the culture solution was changed every 48 hours until confluence of cells was reached. ALP activity of cell lysates was measured by para-nitrobenzene phosphate method. Content of protein in cell lysates was measured by Coomassie brilliant blue method. ALP activity was represented by U/mg of protein and the result was compared with that of control group.

(3) Determination of Mineralization Function $OB_2$ was inoculated into 6 well COSTOR culture plate at a density of $5 \times 10^4$ per well. 24 hours later, the above culture solution was replaced by culture solution containing medicines. Then the solution was changed every 48 hours. 14 days later, the cells were fixed and stained with alizarin red. Mineralization nodules were counted under light microscopy, and the results were compared with those of control group.

Results

1. Influence of Calcium L-threonate on Proliferation of $OB_2$

Tables 1–3 list the results of the test that medicines have influences on cell proliferation.

TABLE 1

Influences of calcium L-threonate and other medicines on osteoblast, test I (unit of concentration: mol/L)

| Group | Calcium L-threonate | Calcium gluconate | $A_{570}$ (X ± SD) Calcium chloride |
|---|---|---|---|
| $10^{-3}$ | 0.458 ± 0.019*** | 0.381 ± 0.052** | 0.325 ± 0.052*# |
| $10^{-5}$ | 0.405 ± 0.085* | 0.351 ± 0.039** | 0.277 ± 0.037 |
| $10^{-7}$ | 0.401 ± 0.082* | 0.267 ± 0.009*& | 0.239 ± 0.005& |
| $10^{-9}$ | 0.387 ± 0.087* | 0.265 ± 0.025 | 0.237 ± 0.005& |
| control | 0.230 ± 0.008 | | |

Note: n = 4, in comparison with control group: *$P < 0.05$, **$P < 0.01$, $P < 0.001$ in comparison with calcium L-threonate group of the same concentration: &$P < 0.05$, #$P < 0.01$

TABLE 2

Influences of calcium L-threonate and other medicines on osteoblast, test II (unit of concentration: mol/L)

| Group | Calcium L-threonate | Calcium gluconate | $A_{570}$ (X ± SD) Calcium chloride |
|---|---|---|---|
| $10^{-3}$ | 0.486 ± 0.010*** | 0.359 ± 0.072**& | 0.423 ± 0.028***& |
| $10^{-5}$ | 0.449 ± 0.041** | 0.301 ± 0.051# | 0.324 ± 0.047& |
| $10^{-7}$ | 0.371 ± 0.047* | 0.268 ± 0.019*& | 0.268 ± 0.022& |
| $10^{-9}$ | 0.418 ± 0.047** | 0.248 ± 0.017& | 0.292 ± 0.023# |
| control | 0.255 ± 0.034 | | |

Note: n = 4, in comparison with control group: *$P < 0.05$, **$P < 0.01$, $P < 0.001$ in comparison with calcium L-threonate group of the same concentration: &$P < 0.05$, #$P < 0.01$

TABLE 3

Influences of calcium L-threonate and other medicines on osteoblast, test III (unit of concentration: mol/L)

| Group | Calcium L-threonate | Calcium gluconate | $A_{570}$ (X ± SD) Calcium chloride |
|---|---|---|---|
| $10^{-3}$ | 0.386 ± 0.024** | 0.229 ± 0.021# | 0.281 ± 0.014# |
| $10^{-5}$ | 0.327 ± 0.034* | 0.242 ± 0.012# | 0.268 ± 0.025& |
| $10^{-7}$ | 0.338 ± 0.048* | 0.233 ± 0.021$ | 0.229 ± 0.09# |
| $10^{-9}$ | 0.316 ± 0.073* | 0.229 ± 0.017 | 0.267 ± 0.016 |
| control | 0.265 ± 0.008 | | |

Note: n = 4, in comparison with control group: *$P < 0.05$, **$P < 0.01$, in comparison with calcium L-threonate group of the same concentration: &$P < 0.05$, #$P < 0.01$, $$P < 0.001$ The data in the Tables 1–3 showed that proliferation rates of $OB_2$ in the $10^{-9}$–$10^{-3}$ mol/L of calcium L-threonate groups in these three tests were all significantly higher than those of control groups, and the OD value of $10^{-3}$ mol/L of calcium L-threonate group was the highest. The OD values of $OB_2$ in calcium L-threonate groups were significantly higher than those of calcium gluconate groups or those of calcium chloride groups. OD values of $OB_2$ of calcium L-threonate groups in test I and test II were significantly higher than those of control groups. In test III, there were no significant differences observed, and OD values of $OB_2$ of most calcium L-threonate groups had no significant differences compared with those of calcium gluconate groups and calcium chloride groups.

2. Influence of Calcium L-Threonate on ALP Activity of $OB_2$

Referring to the proliferation results of $OB_2$, the test that medicines stimulated ALP activity of $OB_2$ was conducted at a concentration of $10^{-3}$ mol/L of the medicines. The results are shown in Table 4.

TABLE 4

Influences of calcium L-threonate and other medicines on ALP activity of osteoblast

| Experiment | 1 | 2 | 3 |
|---|---|---|---|
| Calcium L-threonate | 0.156 ± 0.002* | 0.208 ± 0.003** | 0.164 ± 0.026 |
| Calcium gluconate | 0.115 ± 0.009 | 0.140 ± 0.016 | 0.107 ± 0.025 |
| Calcium chloride | 0.119 ± 0.039 | 0.122 ± 0.08* | 0.102 ± 0.008 |
| control | 0.115 ± 0.016 | 0.151 ± 0.007 | 0.121 ± 0.027 |

Note: n = 4, in comparison with control group: *$P < 0.05$, **$P < 0.01$

At the same concentration, ALP activity of $OB_2$ in calcium L-threonate group was higher than that of control group, among which the increase in test I and test II was significant ($P<0.05$). Compared with calcium gluconate group and calcium chloride group, the ALP activity of $OB_2$ in calcium L-threonate group was increased, however the increase was not significant.

3. Influence of Calcium L-threonate on Stimulating Mineralization Function of $OB_2$ Table 5

TABLE 5

Influences of calcium L-threonate and other medicines on mineralization function of osteoblasts

| Group | Number of mineralization nodules |
|---|---|
| Calcium L-threonate | 12.0 ± 3.742* |
| Calcium gluconate | 6.2 ± 2.588<sup>&</sup> |
| Calcium chloride | 6.4 ± 1.673<sup>&</sup> |
| control | 6.6 ± 2.074 |

Note: n = 4, in comparison with control group: *P < 0.05; in comparison with calcium L-threonate group: <sup>&</sup>P < 0.05.

As can be seen from Table 5, the number of mineralization nodules formed by osteoblasts within two weeks in calcium L-threonate group was the largest, and the increase was significant (P<0.05).

Conclusion

Osteoblasts are bone-forming cells. During bone remolding process, osteoblasts proliferated and differentiated, synthesized and secreted collagen or non-collagen protein which were related with bone formation, thus producing osteoid and promoting mineralization of osteoid. The newly formed bones repaired bone lacuna that was caused by resorbing of osteoclasts. Decline of osteoblast function causes the amount of newly formed bone to decrease, and its ability of repairing bone lacuna attenuates. As a result, bone trabecula becomes thin, weak and perforated, and cortical bone shows porous change. In the pharmacodynamic evaluation of bone formation-promoting medicines on osteoblasts, proliferation rate, ALP activity and mineralization nodules were often used as indexes. These indexes represented the ability of proliferation, differentiation and mineralization of osteoblast respectively. Therefore, these indexes could comprehensively evaluate the stimulation of medicines on the bone formation function of osteoblasts.

The above results showed that: 1) calcium L-threonate had significant stimulation effects on proliferation rate, ALP activity and mineralization nodules formation of osteoblasts cultured in vitro; 2) stimulation effects of calcium L-threonate on the proliferation rate, ALP activity and mineralization nodules formation of osteoblasts cultured in vitro were stronger than those of calcium gluconate or calcium chloride.

EXPERIMENT II

Effect of calcium L-threonate on promoting the synthesis of bone collagen I This study discussed thoroughly the effect of calcium L-threonate on gene expression of collagen I (α-COLI) in osteoblasts cultured in vitro.

MATERIAL AND METHOD

1. Cell Culture: The culture method of primary osteoblast was the same as that of the previous test. $OB_2$ was inoculated at density of $1 \times 10^4$ cells/cm$^2$. In the next day after passage, calcium L-threonate and calcium gluconate with the same concentration ($10^{-3}$ mol/l) were added into different culture flasks respectively, and deionized water with the same volume was added into the control group. Culture medium was changed every 48 hours and the medicines were added. Total RNA of the cells was extracted one week later.

2. Extraction of RNA: The cells were digested with 0.25% trypsin, and were centrifuged at 1000 rpm for 5 min to collect cell pellets. Total RNA was extracted with TRIzol reagent (Gibco Co.) method. Two bands at 18s and 28s were visualized in formaldehyde denaturing agarose gel electrophoresis. The concentration and purity of the RNA were measured by ultraviolet spectrophotometer (the value of A260/A280 falls between 1.7 and 2.0).

3. Reverse transcriptase polymerase chain reaction (RT-PCR): Access RT-PCR System kit (Promega) was used in the test, following the directions of the kit. The RT-PCR of the reaction mixture was performed in PCR analyzer (Bio-Rad Inc.) at 48° C. for 45 min. Inactivate enzyme at 94° C. for 2 min, then 30 cycles of PCR reaction: 30 min at 94° C. for degeneration, 1 min at 54° C. for annealing, 2 min at 72° C. for extension, and after the last cycle, 7 min at 72° C. for another extension. 9 μl PCR products were analyzed in 1.5% agarose gel electrophoresis. Then the bands were analyzed by image analysis system (Image Master VDS). Optical density value was calibrated by internal reference-Actin, and the calibration values were analyzed statistically.

TABLE 6

Sequences of primers

| | Forward primer | Reverse primer |
|---|---|---|
| α-COLI | 5' - cctgccgatgtcgctat- 3' | 5' - gattgggatggagggagtt -3' |
| β-Actin | 5' -ctctatgccaacacagtgc- 3' | 5' - tactcctgcttgctgatcc -3' |

4. Medicines: Each test medicine was formulated at the concentration of 0.1 mol/L, and sterilized by high pressure for later use. Calcium L-threonate, provided by Beijing Juneng Asia Pacific Research Center of Life Science, 1.55 g was dissolved in 50 ml deionized water by heating. Calcium gluconate, Shanghai Huanghai Pharmaceutical Factory, 2.24 g was dissolved in 50 ml deionized water.

Results

The results were shown in Table 7 below. When testing mRNA expression of α-COLI in osteoblast by quantitative RT-PCR, we found that at the same concentration ($10^{-3}$ mol/L) of medicines, the level of mRNA in calcium L-threonate group increased significantly compared with that of control group (P<0.05). The results demonstrated that calcium L-threonate could promote mRNA expression of α-COLI in osteoblast. There was no significant difference of the level of α-COLI mRNA between calcium gluconate group and control group.

TABLE 7

| | Control group | Calcium L-threonate group | Calcium gluconate group |
|---|---|---|---|
| Relative expression amount of α-COLI | 1.0599 ± 0.014 | 1.6989 ± 0.218* | 1.2524 ± 0.377 |

Note: X ± SD, n = 3, in comparison with control group: *P < 0.05

Conclusion

In the process of its proliferation, differentiation and maturation at bone fracture, osteoblasts synthesized a large amount of procollagen I in cytoplasm, which was secreted into matrix, which constituted the main component of bone-collagen, thereby promoting the healing of bone fracture. In addition, the content of bone mass was also an important factor that determined bone strength. The determination of degradation fragments of collagen I was usually used as one of the indexes to reflect bone-forming function. Therefore it showed that calcium L-threonate was very important in preventing or treating bone fracture. Quantitative RT-PCR method used in the present study to detect the level of α-COLI mRNA could reflect the gene expression in OB more accurately than detection of α-COLI protein molecule.

It had been found in the past pharmacodynamics assays that calcium L-threonate could significantly increase bone density, content of bone calcium and biomechanical parameters of emasculated rat. Cell pharmacodynamics test demonstrated that calcium L-threonate could facilitate proliferation, differentiation and mineralization functions of OB. The present study found that calcium L-threonate up-regulated the level of α-COLI mRNA in OB cultured in vitro, which was correlative with the effect reflected by cell pharmacodynamics that it enhanced bone-forming function of osteoblast. It suggested that calcium L-threonate might enhance bone-forming function of OB by enhancing the expression of some genes in OB. It could be further confirmed by the detection of collagen level.

The above tests showed that calcium L-threonate could not only promote proliferation, differentiation and mineralization functions of osteoblast, but also could promote the expression of mRNA procollagen I in osteoblasts cultured in vitro. By these functions, calcium L-threonate could facilitate bone fracture healing, and could increase bone density and mechanical performance as well, so as to prevent bone fracture, especially pathological fracture (such as caused by senile osteoporosis).

That which is claimed:

1. A method for treating bone fracture, comprising the step of administering an effective amount of calcium L-threonate to a subject in need of such treatment.

2. The method according to claim 1, wherein the bone fracture is a traumatic fracture.

3. The method according to claim 1, wherein the bone fracture is a pathological fracture.

4. The method according to claim 1, wherein the calcium L-threonate is administered at a dosage of from about 0.5 to 12 gram/day.

5. The method according to claim 4, wherein the calcium L-threonate is administered at a dosage of from about 3 to 7 gram/day.

6. The method according to claim 1, wherein said calcium L-threonate is administered orally.

* * * * *